(12) United States Patent
Leach et al.

(10) Patent No.: US 9,227,173 B2
(45) Date of Patent: Jan. 5, 2016

(54) METHODS FOR DYNAMIC FILTRATION OF PHARMACEUTICAL PRODUCTS

(75) Inventors: Andrew Michael Leach, Clifton Park, NY (US); Peter Miller, Ledyard, CT (US); Eric John Telfeyan, Delanson, NY (US); David Brandon Whitt, Long Beach, CA (US)

(73) Assignee: General Electric Company, Niskayuna, NY (US)

( * ) Notice: Subject to any disclaimer, the term of this patent is extended or adjusted under 35 U.S.C. 154(b) by 542 days.

(21) Appl. No.: 13/292,468

(22) Filed: Nov. 9, 2011

(65) Prior Publication Data

US 2012/0053364 A1  Mar. 1, 2012

Related U.S. Application Data

(60) Continuation-in-part of application No. 13/081,572, filed on Apr. 7, 2011, now abandoned, which is a division of application No. 11/766,881, filed on Jun. 22, 2007, now abandoned.

(51) Int. Cl.
  *C07C 51/487* (2006.01)
  *B01J 20/26* (2006.01)
  *B01D 15/00* (2006.01)
  (Continued)

(52) U.S. Cl.
  CPC ............ *B01J 20/261* (2013.01); *B01D 15/00* (2013.01); *B01J 20/103* (2013.01); *B01J 20/3204* (2013.01); *B01J 20/3242* (2013.01); *B01J 47/145* (2013.01); *A61M 5/165* (2013.01); *B01D 15/322* (2013.01); *B01D 15/327* (2013.01)

(58) Field of Classification Search
  CPC ....... A61M 5/165; B01D 15/00; B01D 15/08; B01D 15/322; B01D 15/327; B01J 20/26; B01J 20/3242; B01J 20/3204; B01J 47/145; B01J 20/261; B01J 20/103
  USPC .......... 210/665, 669, 691, 692, 766, 774, 807
  See application file for complete search history.

(56) References Cited

U.S. PATENT DOCUMENTS

| 4,673,507 A | 6/1987 | Brown |
|---|---|---|
| 5,039,488 A | 8/1991 | Kohr |

(Continued)

FOREIGN PATENT DOCUMENTS

| JP | 2000351799 A | 12/2000 |
|---|---|---|
| WO | WO2006011809 A1 | 2/2006 |
| WO | WO2006011811 A1 | 2/2006 |

OTHER PUBLICATIONS

Varian Sample Preparation Products, Varian Inc., date unknown, pp. 1-65.

(Continued)

*Primary Examiner* — Matthew O Savage
(74) *Attorney, Agent, or Firm* — John P. Darling

(57) ABSTRACT

A method for dynamic filtration of a pharmaceutical product is provided. The method includes using an unconditioned resin configured to selectively retain one or more components from a mixture having the pharmaceutical product and where the unconditioned resin is configured to be activated by a medium of the mixture. The method further includes the use of at least one positioning material disposed adjacent to the unconditioned resin, where the positioning material is configured to provide mechanical support to the resin to at least partially retain the resin in position.

10 Claims, 10 Drawing Sheets

(51) Int. Cl.
*B01J 20/10* (2006.01)
*B01J 20/32* (2006.01)
*B01J 47/14* (2006.01)
*A61M 5/165* (2006.01)
*B01D 15/32* (2006.01)

(56) References Cited

U.S. PATENT DOCUMENTS

| | | | |
|---|---|---|---|
| 5,091,080 A | | 2/1992 | van Eikeren et al. |
| 5,595,653 A | | 1/1997 | Good et al. |
| 5,882,521 A | * | 3/1999 | Bouvier et al. ............... 210/635 |
| 6,278,893 B1 | | 8/2001 | Ardenkjaer-Larson et al. |
| 6,466,814 B1 | | 10/2002 | Ardenkjaer-Larson et al. |
| 2002/0110495 A1 | | 8/2002 | Hunt et al. |
| 2005/0225328 A1 | | 10/2005 | Ardenkjaer-Larson et al. |
| 2007/0102358 A1 | | 5/2007 | Good |
| 2008/0240998 A1 | | 10/2008 | Urbahn et al. |

OTHER PUBLICATIONS

Majors et al., "Columns for Reversed-Phase LC Sparations in Highly Aqueous Mobile Phases", LC-GC Europe, pp. 2-7, Dec. 2002.

Nagae et al., The Retention Behavior of Reversed-Phase HPLC Columns With 100% Aqueous Mobile Phase:, LC-GC North America, vol. 20, No. 10, pp. 964-968, Oct. 2002.

CA Office Action dated Jun. 17, 2014 from correponding CA Application No. 2690389.

Unofficial translation of KR Office Action issued Apr. 18, 2014 in connection with corresponding KR Patent Application No. 10-2009-7026665.

* cited by examiner

METHODS FOR DYNAMIC FILTRATION OF PHARMACEUTICAL PRODUCTS

CROSS-REFERENCE TO RELATED APPLICATIONS

This application is a continuation-in-part of U.S. patent application Ser. No. 13/081,572, filed on Apr. 7, 2011 now abandoned, which is a Division of Ser. No. 11/766,881 filed on Jun. 22, 2007, which is now abandoned, both of which are herein incorporated by reference.

BACKGROUND

The invention relates generally to methods and devices for filtering pharmaceutical products.

During a pharmaceutical compounding process one or more chemical components are required to be removed from the end product for safety or efficacy purposes. As used herein, the term "chemical components" refers to one or more chemicals present in the initial mixture used to prepare the pharmaceutical product. The chemical components may include any form of compounds intentionally added to, or present from material impurities, or present from contamination of an unrefined pharmaceutical product that are not desired in the end pharmaceutical product. Various methods of filtration and separation are known in the art for removing chemical components from a mixture to obtain a pharmaceutical product that is suitable to be administered to a subject. The conventional removal methods typically require use of solvents or materials that unintentionally add further matter to the mixture that is not desired in the final pharmaceutical product. The undesired matter needs to be removed from the device before conducting the filtration process. This undesired matter may include solvents that are used to prepare the device to perform the filtration or separation or solvents or materials added to the mixture. Alternatively, this undesired matter may also include biologically relevant materials such as endotoxins, proteins, nucleic acids, bacteria or viruses that are contained within the conditioning system or solvents and are subsequently introduced to the filtration device. The additional steps involving addition and subsequent removal of solvents and other materials from the device or the mixture adds to the complexity of the filtration process and to the complexity of the process equipment. Further, these additional steps result in longer time duration for the overall filtration process. Furthermore, quality control mechanisms are required to ensure that the undesired matter is not carried in to the pharmaceutical product. In addition, there is a chance of contamination of the mixture due to extraneous material entering the filtering device while carrying out the steps of administering and removing the undesired matter from the device.

Therefore, there is a need to explore new methods and devices for filtration of pharmaceutical products that do not require addition of solvents or other materials to the filtration device or to the pharmaceutical mixture and that are relatively easier to perform. Further, there is a need for new methods and devices that can be pre-conditioned and stored, such that these devices are ready to use for filtration without conducting any further steps for conditioning the device immediately prior to filtration. Furthermore, there is a need for a device that is sealed to prevent any extraneous material from entering the device either before or during filtration, or once the device is prepared and stored for filtration.

BRIEF DESCRIPTION

In one embodiment, a method of filtering an unrefined pharmaceutical product is provided. The method includes mixing a buffer, a chelator, and one of an acidic medium, a basic medium, or a neutral medium, with the unrefined pharmaceutical product to form a filtering mixture which is comprised of pyruvic acid and an electron paramagnetic agent, and passing the filtering mixture through a filtering device. The filtering device comprises a unconditioned resin configured to selectively retain one or more components from the filtering mixture and wherein the resin is configured to be conditioned in-situ by a the aqueous mixture during the a filtration process.

The filtering device further comprises at least one positioning material disposed adjacent to the resin, wherein the positioning material is configured to provide mechanical support to the resin to at least partially retain the resin in position; and the resin is adapted to retain said one or more components from said aqueous mixture as the pH of the aqueous mixture changes during the filtration process from acidic to basic, or basic to acidic, or from a neutral pH to either acidic or basic, or from an acidic or basic to a neutral pH.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
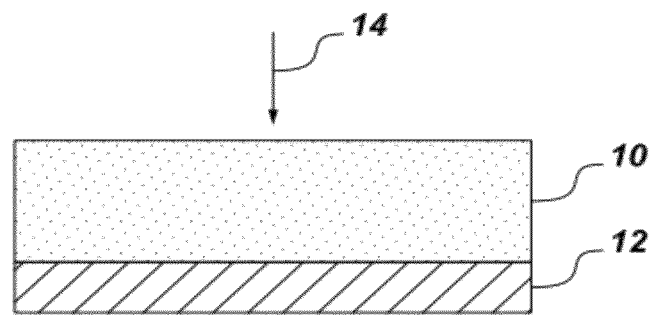
FIGS. 1-2 are cross-sectional side views illustrating alternative arrangements of resins and positioning material, in accordance with aspects of the present technique.

Embodiments of the present technique relate to devices and methods for dynamic filtration of pharmaceutical products to selectively retain one or more components from a mixture of the pharmaceutical product. As used herein, the term "dynamic filtration" refers to the ability of a filtration device to remove or filter one or more components of a mixture having a time varying solubility in a medium of the mixture carrying the pharmaceutical product. As will be described in detail below, the solubility of the components may vary with changing pressure, temperature, volume, pH of the medium, for example. As used herein, the term "pharmaceutical product" includes a compound or a mixture of compounds that are pharmaceutically relevant. The pharmaceutical product may be the end product that is being used. Alternatively, the pharmaceutical product may be an intermediate product formed while making a pharmaceutical compound. The one or more components that are selectively retained by the filtration device are generally impurities or undesired compounds present in the pharmaceutical product that are not desired in the end product. The one or more components may be by-products formed from a reaction involving two or more reactants used to form the pharmaceutical product, for example.

As will be appreciated, typically, a process of filtering a pharmaceutical product requires an additional step of conditioning the filtration device immediately prior to passing the mixture having the pharmaceutical product through the device. In conventional filtration devices, which are employed for filtering a pharmaceutical mixture, conditioning of the device prior to filtering often involves the use of additional chemicals in the form of conditioning agents or solvents. As used herein, the term "conditioning" refers to a modification of one or more parts of the filtration device, such that the one or more parts are configured to retain the impurities or chemical components from the mixture after undergoing the modification. Non-limiting examples of modification may include wetting a surface of a resin, creating conditions in the resin that allow the chemicals to be filtered to interact with the surface of the resin, or creating a liquid/solid interface from a solid/gas interface. For example, some conventional devices are conditioned using alcohol. The alcohol added for conditioning step needs to be subsequently removed to filter the pharmaceutical product. In addition, the solvent or other materials used for conditioning are typically not desired in the end product, therefore, this undesired matter needs to be removed from the filtration device once the device is conditioned, and before the filtration process begins. The removal of such chemicals requires extra process steps, and hence, more process time.

Further, the conditioning at the point-of-use may cause the potential problem of having biologically relevant materials introduced into the system from the onsite conditioning process (i.e. through solvents and water). Also, in systems requiring conditioning of the filter at the point-of-use, the additional steps of removing the solvent from the filter are integral part of the filtration step and contribute to prolonging the filtration process. The additional steps lead to prolonged process of manufacturing the pharmaceutical product, also, sometimes due to limitation on time, or the number of process steps, or the complexity of the process, it may not be possible to entirely separate out the conditioning agent from the pharmaceutical product, thereby resulting in a contaminated pharmaceutical product. Accordingly, elimination of conditioning step just prior to filtration prevents the administration of these unwanted conditioning agents, prevents the use of additional steps otherwise required to separate out the conditioning agents and other chemicals added to facilitate conditioning of the device prior to filtration, and greatly reduces the risk of introduction of unwanted biologically relevant materials. As will be described in detail below, the filtration devices of the present technique do not require addition of undesired matter either during or just prior to filtration. Accordingly, the filtration devices of the present technique do not require additional steps otherwise employed in conventional filtration devices to remove the earlier administered undesired matter prior to carrying out the filtration of the mixture. In one embodiment, the filtration device is configured to be conditioned during filtration. In another embodiment, the filtration device is preconditioned and stored under controlled conditions prior to filtration.

In some embodiments, the filtration device is configured to be conditioned by the medium of the pharmaceutical mixture. As will be described in detail below, in these embodiments, the filtration device includes an unconditioned resin that is activated by the medium of the mixture during the filtration process. The activated resin is configured to selectively retain one or more components from a mixture comprising the pharmaceutical product. Therefore, by employing the device of the present technique, the additional steps involving conditioning the device prior to filtration become redundant. A combination of unconditioned resin and medium may be chosen depending on their mutual compatibility. Further, the medium may be chosen such that the medium may be easily separated from the pharmaceutical product. Alternatively, the medium may be chosen such that the medium may be retained in the final pharmaceutical product, without contributing to any deleterious effects to the pharmaceutical product.

The mixture of the pharmaceutical product may include a medium such that the unconditioned resin is configured to be in-situ conditioned by the medium or the filtration mixture. In other words, the device is configured to filter the one or more components from the mixture without being conditioned prior to filtration. In its activated state, the resin is configured to filter out the one or more undesired components from the mixture of the pharmaceutical product by retaining the undesired components and allowing the rest of the mixture to pass through the resin. The resin may be configured for chemical retention, mechanical retention, or both of the one or more components of the pharmaceutical mixture. In certain embodiments, the resin material is a porous material. In these embodiments, the resin material has a higher surface area, and therefore higher chemical filtration efficiency.

An unconditioned resin may be distinguished over resins that are typically used for example in reversed phase or normal type chromatography. For example in reverse phase, silica and nonpolar type media may be conditioned with a water-miscible organic solvent such as methanol, followed by water or an aqueous buffer. In normal phase SPE silica and polar adsorption media may be conditioned with an organic solvent.

In certain embodiments, the unconditioned resin may be a type of silica including, but not limited to various C18 or C8 functionalized silica based chromatographic resins. Representative commercial resins include those such as YMC® ODS-A (YMC Europe GMBH, Dinslaken Germany) which has lipohilic C18 chains, Phenomenex® Sepra C18-T (Phenomenex, Torrance Calif.), Alltech® Large Pore C18 (Alletech Associates, Inc, Deerfield, Ill.), Varian Polaris® (Huijie Scien-Tech Development Co, LTD, Shanghai, China), Hamilton PRP-3® (Hamilton, Reno, Nev.) Agilent® BondElut C18 (Agilent Technologies, Santa Clara Calif.), Alltech® C8, and Agilent Bond Elut C8.

In other embodiments the unconditioned resin may be a polymeric resin, such as, but not limited to a water wetatable resin such as Waters Oasis® HLB (Waters Corporation Milford, Mass.) which is an N-vingylpyrolidone-divenylbenzened copolymer and Phenomenex® Strata X which is a modified styrene divinylbenzene polymer.

Characteristics such as particle size, particle shape, and packing efficiency of the unconditioned resin material may affect the ability of the resin bed to remove particulate. In mechanical filtration, the particle size of the particulates that need to be filtered out are likely much larger than the pore size of the resin materials. In one embodiment, the pore size of the resin is in a range from about 60 A° to about 4000 A°.

In some embodiments, the unconditioned resin is adapted with surface modification. The choice of the unconditioned resin materials may vary depending on whether the unconditioned resin is configured to be activated by the medium of the mixture, or whether the unconditioned resin is pre-activated and stored in the device. In embodiments where the unconditioned resin is configured to be activated by the medium, it is required to have the unconditioned resin that contains suitable polar/hydrophilic functionalities. For example, the surface of the particulate that comes in contact with the mixture, the bulk (or substrates) of the unconditioned resin may be modified with one or more non-polar functionalities, or a combination of a non-polar and polar functionalities such that the modified surface can be activated by the medium. Typically, the substrates may be polymer based. The polar functionalities are chosen such that they allow the medium to activate the unconditioned resin but do not negatively impact the retention of the one or more components by the hydrophobic functionality of the resin. In case of filtration devices where the unconditioned resin is configured to be activated by the medium of the mixture, the medium of the mixture may be aqueous based. The aqueous based medium may be neutral, basic or acidic in nature. In certain embodiments, the aqueous based medium may change dynamically from acidic to basic, or basic to acidic, or from a neutral pH to either basic or acidic condition, or from an acidic or basic condition to a neutral pH. When the pharmaceutical mixture is passed through the device, one or more of the components are trapped by hydrophobic and/or polar functionalities in the resin and hence, selectively retained. The rest of the mixture is allowed to pass through the device.

In some embodiments, the unconditioned resins may be activated based on the morphology. The resin may have suitable morphology, such that the resin can be wet by an aqueous based medium, for example. As will be appreciated, it is desirable for the resin to have hydrophobic character to retain the impurities, and be compatible with the mixture to be filtered. In certain embodiments, the resins may include pores that are of the sizes such that upon application of pressure, the pores allow the medium of the pharmaceutical mixture to wet the resin surface allowing interaction of the chemical components to be filtered from the pharmaceutical mixture with the resin's functionality. In these embodiments, the pores of the resin may be wet by the medium even in the absence of hydrophilic moieties on the resin. In one embodiment, pressure is used in addition to large pore size resin to achieve wetting. The pressure in this case is the fluidic pressure of the pharmaceutical mixture being introduced into the device. In an exemplary embodiment, a flow rate of the mixture at the filtering device is in a range from about 3 mL/s to about 12 mL/s. In another embodiment, an additional pressure may be required to activate the resin.

In embodiments where the filtration device is pre-conditioned and stored for later use, the filtration device is pre-conditioned with a solvent, such as an alcohol, to activate the resin, the filter is then flushed with water to remove the solvent. In one embodiment, ethanol may be used as the solvent for conditioning the filter. The advantage of employing ethanol is that usually the pharmaceutical product has tolerance levels for ethanol. The pre-conditioned filtration devices may be directly used at the time of filtration without having to conduct any further steps related to conditioning, thereby reducing the overall time for filtration. In these embodiments, the resin is activated and stored in the device prior to filtration. The resin may be activated using solvents or other conditioning materials. If the solvents or the other conditioning materials are not desired in the end product, the filtration device may be processed or washed to remove the solvents or the other conditioning materials from the device.

In certain embodiments, the pre-conditioned device is preserved by bringing the temperature of the device below the freezing point of the solvent left in the device. For example, in case of hydrophobic resins because a de-wetting process occurs where the water is expelled from the pores over time and hence the resin may loose its efficiency, freezing the solvent facilitates storing the filters with solvent in them. In case of pre-conditioned filters, the additional steps required to separate out the conditioning chemicals/solvent from the filter prior to filtration are carried out before storing the device. Hence, these additional steps do not contribute to prolonging the filtration process.

In some embodiments, the unconditioned resin may be activated during the manufacturing of the filtration device. Once the device is activated, in some cases the solvents are removed, the device may then be sealed to prevent contaminants, such as biologically relevant materials, from entering the system. In embodiments where water acts as the solvent, it may not be required to remove the solvents prior to sealing the device. Once conditioned and stored, the pre-conditioned device acts as a ready-to-use device that may be directly used for filtration without performing any conditioning steps prior to filtration. In one embodiment, the filtration device may be sterilized to remove any biologically relevant material, for example. In one embodiment, the pre-conditioned device is hermetically sealed to retain the sterility prior to and during filtration. It should be noted that similar to pre-conditioned devices, the filtration devices where the resin is configured to be in-situ conditioned by the medium or the filtration mixture may be hermetically sealed to prevent any extraneous material from entering the device either before or during filtration. The pre-conditioned filter works with many different resins that have a hydrophobic character. The resin retains the one or more components and is compatible with the medium/mixture to be filtered. Examples of such resins include Silica based $^{18}C$ used in solid phase extraction, or resins employed in flash chromatography applications.

Further, the device includes at least one positioning material disposed adjacent to the resin, where the positioning material is configured to provide mechanical support to the resin to at least partially retain the resin in position. Additionally, the positioning material may be configured to at least partially retain one or more components from the pharmaceutical mixture. The positioning material may be made of a material that is inert to any solvents, medium, or pharmaceutical components in the mixture. Further, for healthcare application, the positioning material must be suitable for use in medical devices where it comes into contact with a pharmaceutical product. In certain embodiments the positioning material may include a frit, a membrane, a screen, a fiber bed, any other mechanical support. The positioning material may either be a continuous structure or may be a patterned structure. For example, the positioning material may be a continuous porous plate, or may be in the form of a grid. In some embodiments, the positioning material itself may be configured to selectively retain one or more components from the pharmaceutical mixture. In one embodiment, the positioning material may retain the one or more components mechanically. For example, the positioning material may be a porous material having pores smaller than the particles of the component to be retained. For example, the pore size of the positioning material is in a range from about 5 micrometers to about 30 micrometers. In another embodiment, the positioning material may be configured to chemically retain the one or more components from the pharmaceutical mixture. The positioning material may be made from materials including but not limited to, hydrophobic and hydrophilic porous polymers including polyethylene and Teflon™ that may be used in medical applications without reacting with the medium or pharmaceutical product.

As will be described with regard to FIGS. 1-2 and 4-10, the resin and the positioning material may be arranged in several different configurations. In some embodiments, the resin may be configured for chemical retention of some components, while the positioning material may be configured for mechanical retention of same or different components. The resin and the positioning material may be complimentary to each other in terms of retaining the one or more components, for example the resin may retain the soluble undesirable components from the mixture and the positioning material may retain insoluble components from the mixture. Alternatively, the resin and the positioning material may be configured to retain the same one or more components. In these embodiments, the positioning material may be used as a back up arrangement to retain the components left by the resin and visa versa.

In one embodiment, the pharmaceutical mixture may include species that are soluble in the medium. In this embodiment, the resin is configured to retain the soluble species. In another embodiment, the pharmaceutical mixture may include species that are insoluble in the medium. In this embodiment, the positioning material and/or the resin are configured to retain the insoluble species that are to be separated/extracted from the mixture. In another embodiments, some of the species may be soluble while others may be insoluble in the medium. In certain embodiments, the device is configured to retain both soluble and insoluble species from the pharmaceutical mixture. In this embodiment, the positioning material and/or the resin is configured to retain some of the insoluble species while the resin is configured to retain the soluble species to be separated from the pharmaceutical mixture. Further, in some embodiments, the solubility of some of the species in the pharmaceutical mixture may vary with time as a function of the conditions of the media including pH, polarity, concentration, and temperature. In these embodiments, the resin or the positioning material or both may be configured to retain the species having time varying solubility. In these embodiments, the positioning material and/or the resin retain the insoluble components during certain phases of the filtration process. As the solubility of the components is modified by the properties of the solution, the insoluble materials become soluble and re-enter the solution. These re-solubilized components are then retained on the resin.

For example, in case of a mixture of electron paramagnetic agent (EPA) and pyruvic acid, the EPA is initially insoluble and retained by the positioning material. Subsequently, when the EPA becomes soluble, the EPA may be removed by the activated resin. An advantage of this method is that the dynamic solubility of the EPA may be controlled by modifying the composition of the medium and/or varying the dissolution conditions which may include one or more of a pressure and temperature. For example, in varying the composition of the medium, filtration of particulate EPA is possible when an aqueous dissolution maintains pH below the pKa of pyruvic acid. While EPA is soluble in neat pyruvic acid, it is insoluble in an aqueous solution of pyruvic acid.

The volume (or weight) ratio of the resin and the positioning material are selected for the given application or intended use. In one example, a pharmaceutical mixture in the range of about 1 gram to about 2 grams requires a resin in a range from about 3 grams to about 10 grams.

Further, the device also includes a filter body to house the arrangement of the resin and the positioning material. The filter body may be of various shapes and sizes depending on the requirements of filtration. For example, the filter body may have provisions for mixing a medium to the pharmaceutical product to form a pharmaceutical mixture. In another embodiment, the filter body may have provisions for varying the flow of a mixture of the pharmaceutical product to the resin. As will be described with regard to FIGS. 4-10, in some embodiments, the filter body may have a plurality of arrangements of resin and positioning materials. In these embodiments, each of the plurality of arrangements may have the same configuration of the resin and the positioning material. Alternatively, some or all of the plurality of arrangements may have configurations that are different from others.

In some embodiments, the device may also include a diffuser configured to distribute the mixture into a plurality of streams. The diffuser is used before the positioning material to evenly distribute the mixture over the entire face of the positioning material. The diffuser may be employed to homogenize the mixture prior to the mixture being filtered by the resin. As with the positioning material, the diffuser may be made of a material that is inert to any solvents, medium, or pharmaceutical components in the mixture.

In certain embodiments, the device as disclosed is described in context of nuclear magnetic resonance (NMR) analysis, and particularly with regard to magnetic resonance imaging (MRI). It should be noted that the techniques described herein may be applied in various other systems other than the MRI. Also, the device may be employed to use pharmaceutical compounds other than the one employed in MRI.

MRI and NMR spectroscopy lack sensitivity due to the normally very low polarization of the nuclear spins of the samples used. A number of techniques exist to improve the polarization of nuclear spins in the solid phase. These techniques are known as hyperpolarization techniques and lead to an increase in sensitivity. As used herein, the term "polarize" or "polarization" refers to the modification of the physical properties of a solid material for further use in MRI. Further, as used herein, the term "hyperpolarized" refers to polarized to a level over that found at room temperature and 1 T, which is further described in U.S. Pat. No. 6,466,814. In hyperpolarization techniques, a sample of an imaging agent, for example $^{13}C$ pyruvate or another similar polarized metabolic imaging agent, is introduced or injected into the subject being imaged. Typically, $^{13}C$ pyruvate is mixed with tris(8-carboxyl-2,2,6,6-tetra(2-(1-methoxy-2,2-d2-ethyl))-benzo[1,2-d:4,5-d']bis(dithiole-4-yl)methyl sodium salt, more commonly known as electron paramagnetic agent (EPA) to enhance the polarization of $^{13}C$. As will be appreciated, EPA, a processing agent needs to be removed from the pharmaceutical product before administering the product in the subject.

In one example, where a 100 ml of pharmaceutical product is being formed, approximately 10 to 50 micromoles of EPA are added to the pyruvic acid. Assuming no filtration, this amount of EPA results in an EPA concentration of 100 to 500 micro-molars in the dissolution product. It is desirable to have EPA concentration less than or equal to permitted levels in the dissolution product, corresponding to a high filtration efficiency. For example, the filtration device may be greater than about 90 percent. Accordingly, it is required to bring down the concentration of EPA to an allowable limit in the product following polarization and dissolution of the frozen pyruvic acid sample. In the presently contemplated embodiment, EPA is at least partially filtered out using the filtration devices of the present technique.

EPA exhibits solubility that varies with pH. At pH less than 4, EPA is predominantly insoluble and forms particulate with diameter greater than or equal to 10 microns. Above pH 4, EPA is soluble in aqueous solutions.

In certain embodiments, pyruvic acid and EPA are initially located in a small vial in a frozen state. An aqueous solution, known as the dissolution media, is used to melt the pyruvic acid and EPA and carry it through a filter to a final receiving vessel. This dissolution media can also be used to modify the pH of the product as needed. Because of the time associated with the melting process, the liquid arriving at the filter can at any given time have varied acid and EPA concentration as well as pH ranging from 2-12. These concentration and pH profiles vary as a function of time during the dissolution process.

In methods and devices in accordance with the present invention, a solid sample of the frozen pyruvic acid and EPA can be polarized while in the solid phase by any appropriate known method, e.g. brute force polarization, or dynamic nuclear polarization, while being maintained at a low temperature (e.g. under 100 K) in a strong magnetic field (e.g. 1-25 T). After the solid sample has been polarized, it is melted with a minimum loss of polarization. In the following the expression "melting means" will be considered to mean the following: a device capable of providing sufficient energy to the solid polarized sample to melt it or otherwise bring the polarized sample into solution for introduction into the subject being imaged. As used herein, the term "solid" refers to solid materials; semi-solid materials or any combination thereof provided the material requires some transformation to attain a liquid state suitable for introduction into a subject being imaged.

Turning now to FIG. 1, a resin is disposed in the form of a layer 10. A positioning material 12 is disposed on one side of the resin 10 in a direction of a flow of a stream of the mixture as represented by arrow 14. Typically, the positioning material 12 is configured to provide mechanical support to the resin 10 to at least partially retain the resin 10 in its position. The positioning material 12 may be a continuous layer. Although not illustrated, the positioning material 12 may include patterned structure. For example, the positioning material 12 may be a grid, or a plurality of rods, a frame. As described above, in some embodiments, the positioning material 12 may also be employed to assist the resin in selectively retaining one or more components from the mixture.

Figure 2:
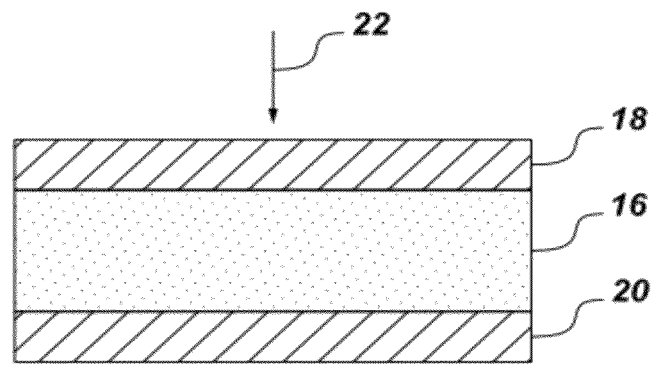

FIG. 2 illustrates an alternate embodiment of the arrangements of the resin and positioning material of FIG. 1. In the illustrated embodiment, the resin 16 includes positioning materials 18 and 20 on either side of the resin 16 in the direction of flow of the mixture as illustrated by the arrow 22. As described with regard to FIG. 1, the positioning materials 18 and 20 may have solid or non-solid patterns. Further, the configuration of the illustrated embodiment may be repeated. In other words, the device may employ a stack having a plurality of resins 16, disposed between a plurality of positioning materials 18 and 20. In one embodiment, the positioning material 18 may be configured to act as a diffuser. Generally, the resin is tightly packed against the positioning material. However, a distance between the top of the filter body and the diffuser/positioning material may be desired in some cases. For example, in case of a filter body employing a plurality of resin-positioning material pairs, the distance between the positioning material of one pair and the resin of the adjacent pair may allow for remixing of product prior to the next resin bed. This approach may also be beneficial in situations where the previous resin bed has been locally saturated with the chemical component (e.g., EPA) to be filtered causing bleed through while other areas remain unsaturated. This situation may arise if the diffuser did not evenly distribute flow, for example. Hence, the spaces allows for redistribution of the mixture. As will be described with regard to FIG. 7, a separate diffuser plate may also be applied in addition to the positioning materials 18 and 20.

Figure 3:
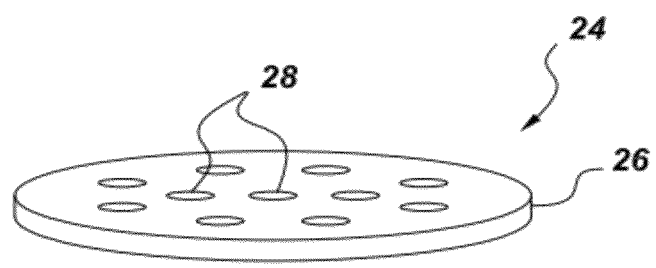
FIG. 3 is a perspective view of a diffuser employed in the filter configuration of FIG. 2.

FIG. 3 illustrates a perspective view of a diffuser 24 that may be employed in place of or in addition to the positioning material 18. The diffuser 24 includes a plate 26 having a plurality of through holes 28. The mixture is distributed into a plurality of streams, which pass through the holes 28. The streams eventually unite within the resin, for example resin 16, as shown in FIG. 2.

Figure 4:
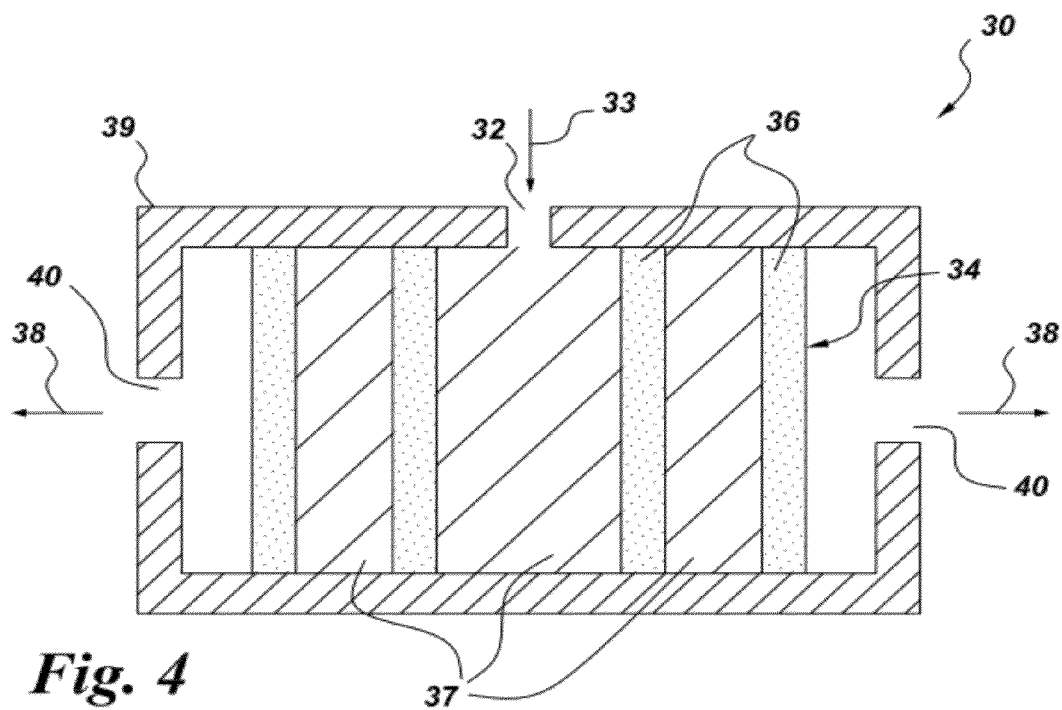
FIGS. 4-8 are schematics illustrating an exemplary filtering devices for filtering of a pharmaceutical product, in accordance with aspects of the present technique.

FIG. 4 illustrates an exemplary filtration device 30 having an inlet 32, the direction of flow of the mixture at the inlet 32 is represented by the arrow 33. The device 30 includes a layered structure 34 having alternate arrangements of layers of positioning material 36 and resins 37. The direction of flow of the filtered mixture is illustrated by arrows 38 exiting out of the filter body 39 through the outlets 40.

Figure 5:
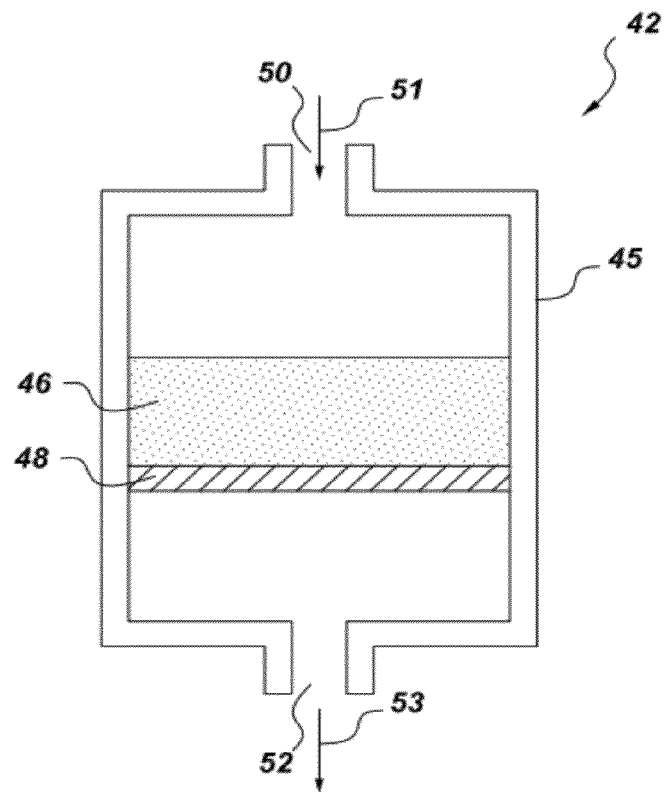

FIG. 5 illustrates a filtration device 42. The filtration device 42 may employ any combination of the configurations or parts of FIGS. 1-2, or their derivatives. In the presently contemplated embodiment, the device 42 includes an arrangement 44 having a resin 46 disposed on a positioning material 48. The device 42 further includes a filter body 45 having an inlet 50 and an outlet 52 for the mixture to enter and exit the device 42, as represented by arrows 51 and 53, respectively.

Figure 6:
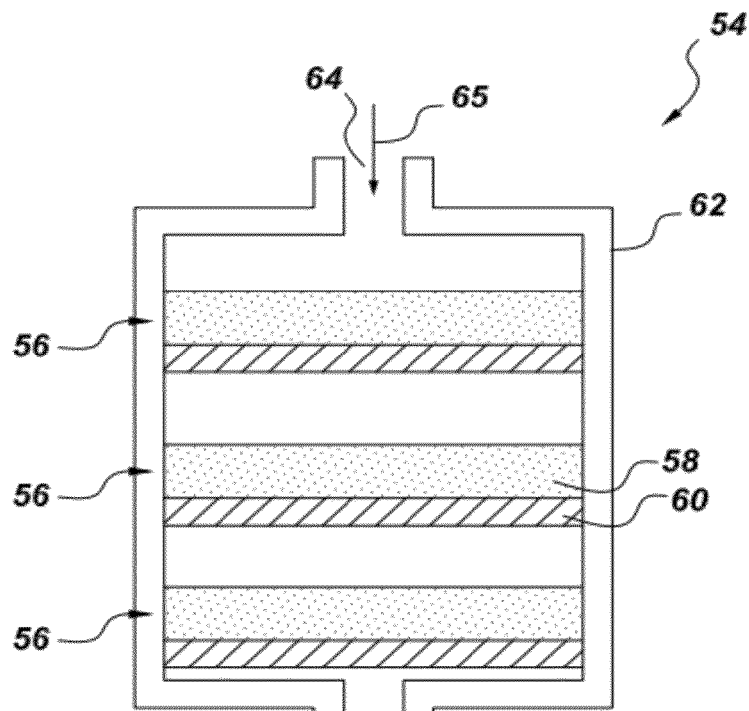

FIG. 6 illustrates an alternate embodiment of the device 42 of FIG. 5. In the illustrated embodiment, the device 54 includes a plurality of arrangements 56 disposed within the body 62. Each of the plurality of arrangements 56 may or may not be identical. In the illustrated embodiment, each of the configurations 56 includes a resin 58 and a positioning material 60. Further, the body 62 includes an inlet 64 and an outlet 66 for entry and exit of the mixture as represented by arrows 65 and 67, respectively.

Figure 7:
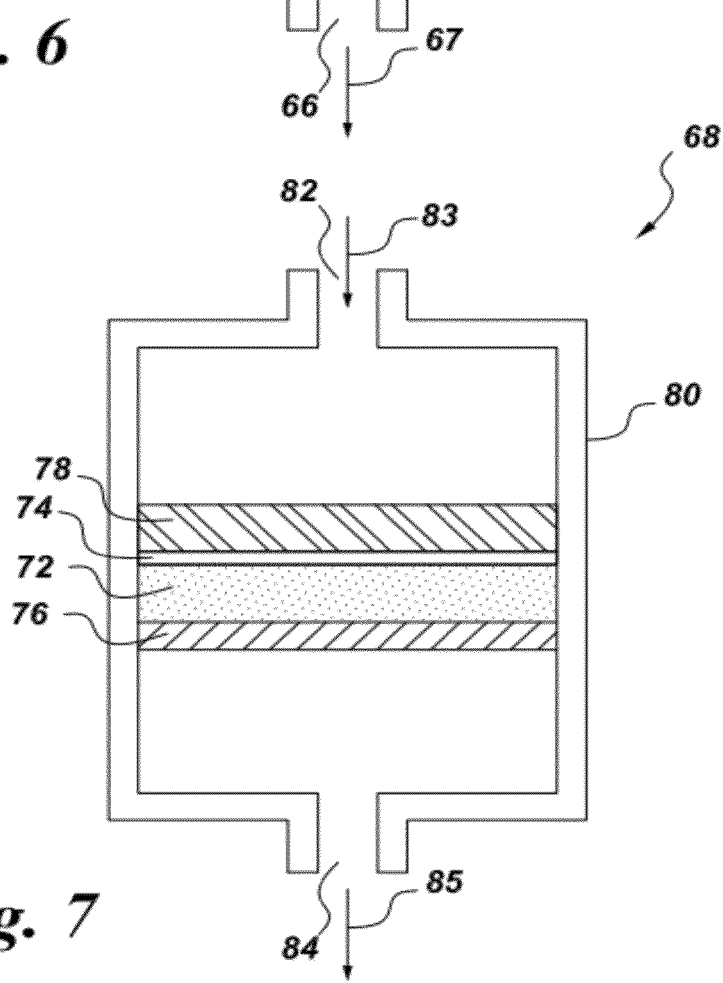

FIG. 7 illustrates yet another embodiment of the devices 42 and 54 of FIGS. 5 and 6, respectively. In the illustrated embodiment, the device 68 employs a resin 72, positioning materials 74 and 76. The device 68 further includes a diffuser 78. Further, the device 68 includes a filter body 80 having inlet 82 and an outlet 84, for directing the flow of the mixture as illustrated by arrows 83 and 85, respectively.

Referring further to FIG. 7, in one embodiment, the pharmaceutical mixture has a time varying pH gradient, such as found in pyruvate and EPA mixture. Initially, the pH of the mixture tends to be acidic and with time the pH increases and shifts towards neutral or basic. In this embodiment, a filter containing a resin 72 disposed between entrance and exit positioning materials 74 and 76 is employed. Additionally, a diffuser 78 is used before the entrance positioning material 74 to evenly distribute the liquid over the entire surface of the resin 72. In this embodiment, the pyruvic acid and EPA are dissolved with an aqueous solution that has a basic pH, such as water containing sodium hydroxide. In addition, other pH modifiers or buffers may also be added to the pharmaceutical mixture. In a further embodiment, where the pharmaceutical mixture comprises pyruvic acid and EPA undergoing hyperpolarizatoin, as the pyruvic acid melting process commences, the ratio of acid to base in the solution above the frozen pyruvic acid and EPA is dominated by the acid and therefore the pH of the solution is acidic. Under this condition, the solution that is initially filtered has a pH<4, making EPA insoluble. At this time the EPA, being an insoluble particulate, is trapped on the entrance positioning material 74 or on the front surface of the resin bed 72. At the same time the pyruvic acid aqueous solution passes through the entrance positioning material 74, enters the resin bed 72, wetting and thus activating the resin 72, passes through the exit positioning material 76 and exits the filter. As the dissolution continues, the ratio of acid to base in the vial decreases, causing a shift in the pH of the liquid leaving the vial to more neutral or basic pH. As the mixture arrives at the filter, EPA, either in the liquid or having been previously trapped on the entrance positioning material 74 or front the resin bed 72, becomes soluble and enters the resin bed 72. Within the resin bed 72, the soluble EPA is retained on the activated resin 72, while the pyruvic acid and sodium pyruvate pass through the filter to the receiving vessel.

Figure 8:
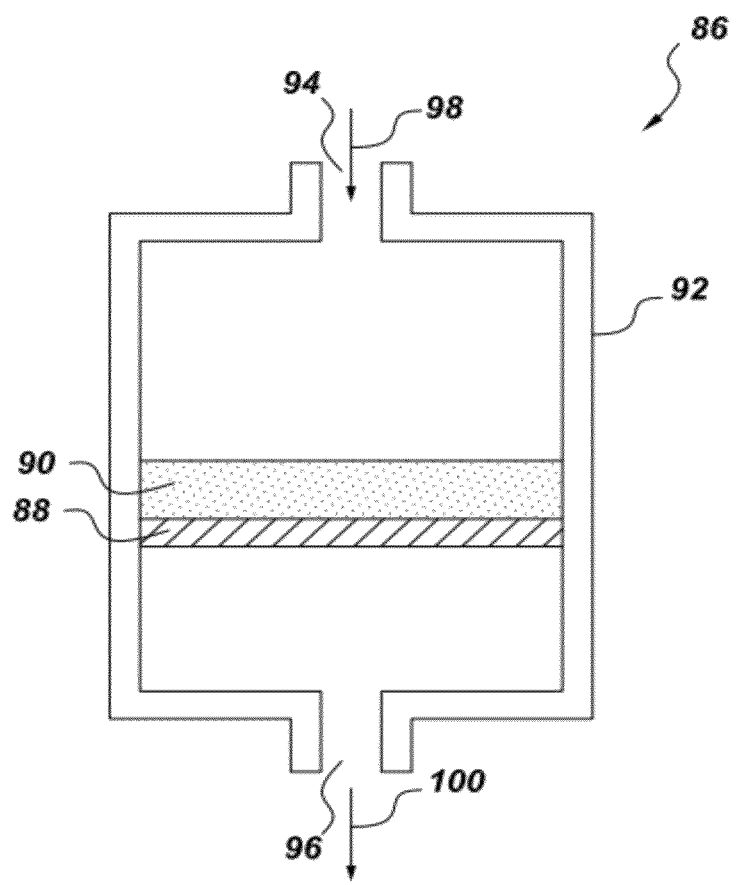

Turning now to FIG. 8, a filtering device 86 includes a positioning material 88 and a diffuser 90 disposed over the positioning material 88 in the direction of flow of the mixture. The device 86 does not include a resin. Such a device 86 may be employed in cases where the pharmaceutical mixture contains only insoluble species that need to be separated out from the pharmaceutical product. The device further includes an inlet 94 and an outlet 96 and the direction of flow of the mixture in the device 86 is illustrated by arrows 98 and 100.

In the illustrated embodiment of FIG. 8, the pH of the mixture may be in the acidic range. In one embodiment, a device 68 containing only positioning material 88 without a resin bed is employed. A diffuser 90 is used before the positioning material 88 to evenly distribute the mixture over the entire face of the positioning material 88. In this embodiment, the pyruvic acid and EPA are dissolved with an aqueous solution that has a neutral pH, such as pure water. Under this condition, the solution that is initially filtered has a pH<4, making EPA insoluble. At this time the EPA, being an insoluble particulate, is trapped on the positioning material 88. At the same time the pyruvic acid aqueous solution passes through the positioning material 88. Subsequently, the pyruvic acid is neutralized to form sodium pyruvate within a receiving vessel.

Figure 9A:
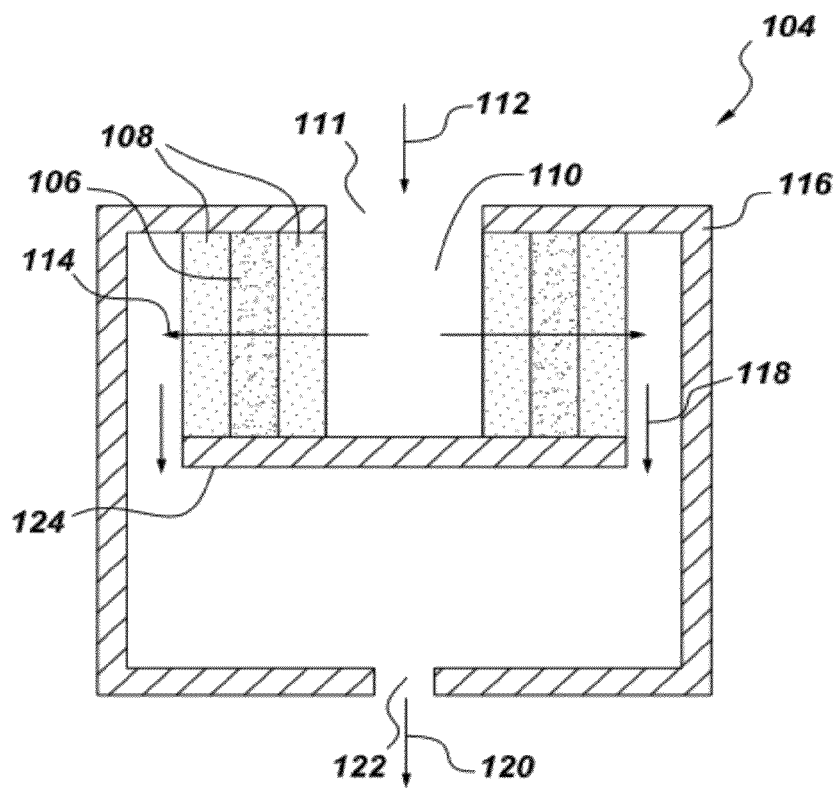
FIG. 9A is a cross-sectional side view illustrating a radial filtration device for filtering of a pharmaceutical product, in accordance with aspects of the present technique.
Figure 9B:
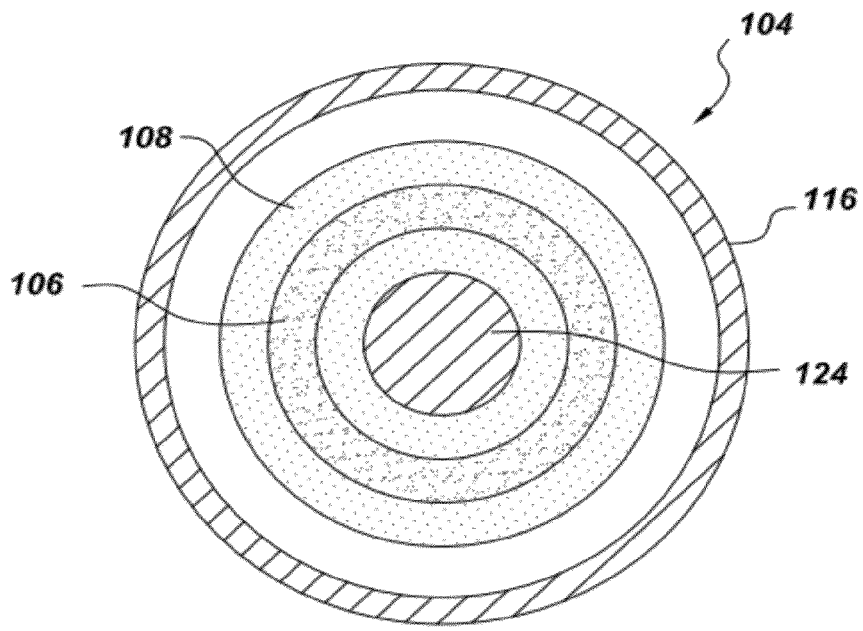
FIG. 9B is a top view of the radial filtration device of FIG. 9A.

Turning now to FIG. 9A, a radial filtration device 104 is illustrated. FIG. 9B illustrates the top view of the device 104. The resin material 106 and the positioning material 108 are co-centrically arranged around the passage 110 for mixture entry through the entry 111. Such a filtration device 104 may be employed in filtration applications where the mixture enters the device 104 at a high flow rate. Also, the filtration device 104 may be employed for large-scale filtration applications. The mixture enters the passage 110 in a direction illustrated by the arrow 112, and is distributed in radial direction (as illustrated by the arrows 114) owing to the incoming mixture pressure and the arrangement of the resin and the positioning materials. The filtered mixture then percolates through the resin material 106 and the positioning material 108 to enter the passage between the walls of the filter body 116 and the arrangement of and the resin material 106 and the positioning material 108 as illustrated by the arrows 118. The mixture then exits (arrow 120) through the exit 122 of the filter body 116 by passing through a passage between the walls of the filter body and the support plate 124 holding the arrangement of the resin material 106 and the positioning material 108. Although not illustrated, in an alternate arrangement, the filtering device may also function if the mixture path is represented by reversing the direction of arrows 112, 114, 118 and 120 by 180°. That is, the mixture to be filtered is entered into filter body 116 through location 122 and moves through the passage between the walls of the filter body 116 and the arrangement of the resin material 106 and the positioning material 108. The mixture then enters the arrangement of the resin material 106 and the positioning material 108 to be filtered. The filtered mixture is collected at location 111.

Figure 10:
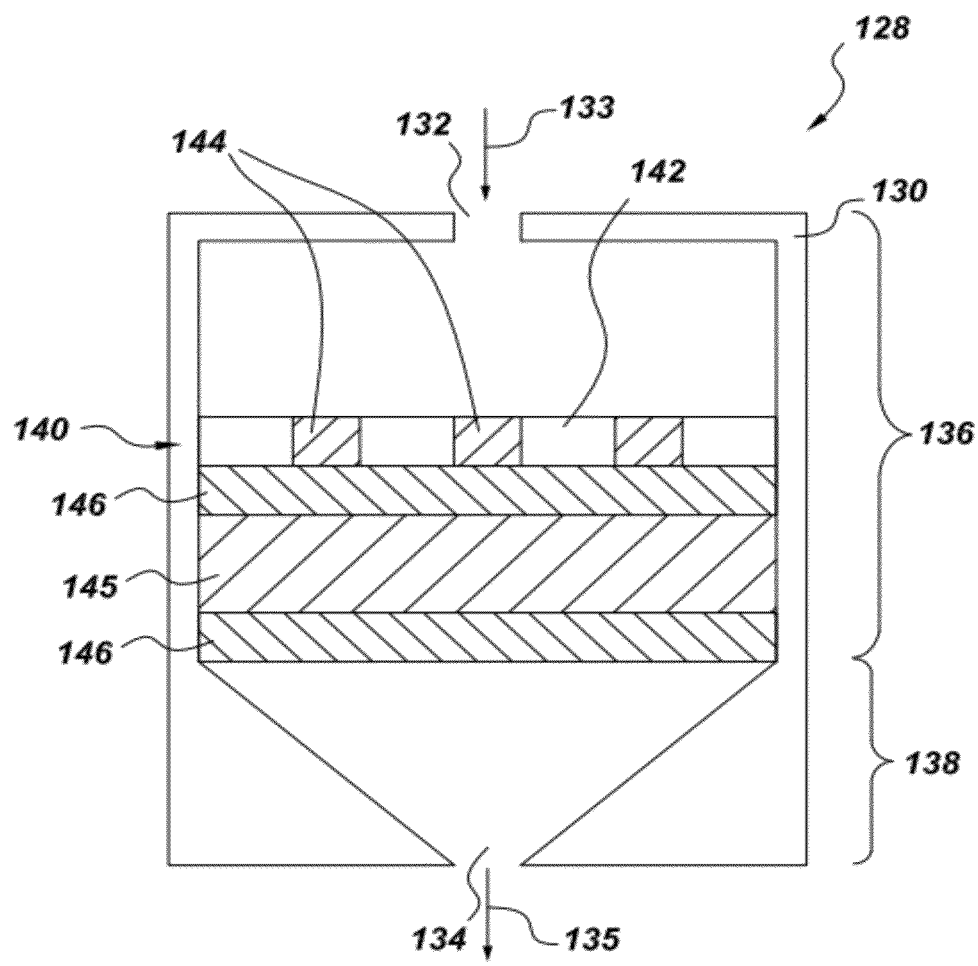
FIG. 10 is a cross-sectional side view of a filtering device having a conical shape at the exit location.

Turning now to FIG. 10, a filtering device 128 having a filter body 130, an inlet 132 and an outlet 134 is illustrated. Arrows 133 and 135 represent the direction of flow of the mixture. A portion 136 of the filter body 130 has a cylindrical cross-section, while the rest of the portion 138 of the filter body 130 has a conical shape. The conical shape of the portion 138 facilitates easy exit of the mixture from the filter body 130 following filtration. The filtration device 128 further includes a diffuser 140 having a substrate 142 with holes 144. The filtration device 128 also includes a resin material 145 disposed between two positioning materials 146.

In certain embodiments, an unrefined pharmaceutical product is mixed with a basic medium, a buffer and a chelator to form a filtering mixture. For example, the unrefined pharmaceutical product may include pyruvic acid, and electron paramagnetic agent. The basic medium may include sodium hydroxide, the buffer may include tris(hydroxymethyl)-aminomethane (TRIS). The presence of chelator may facilitate separation of metal ions from the mixture. The mixture is then entered into the filter body via the inlet. Once inside the filter body, the mixture passes through the resin and the positioning material, and exits the device via the outlet.

In certain embodiments, the filtration device, such as the device 42 or 54 may be employed in nuclear magnetic resonance (NMR) analysis, particularly to nuclear magnetic resonance imaging (MRI) and analytical high-resolution NMR spectroscopy. For example, the device may be employed for filtration of polarizing materials prior to their administration in the body of a patient for the purpose of magnetic resonance imaging (MRI).

Figure 11:
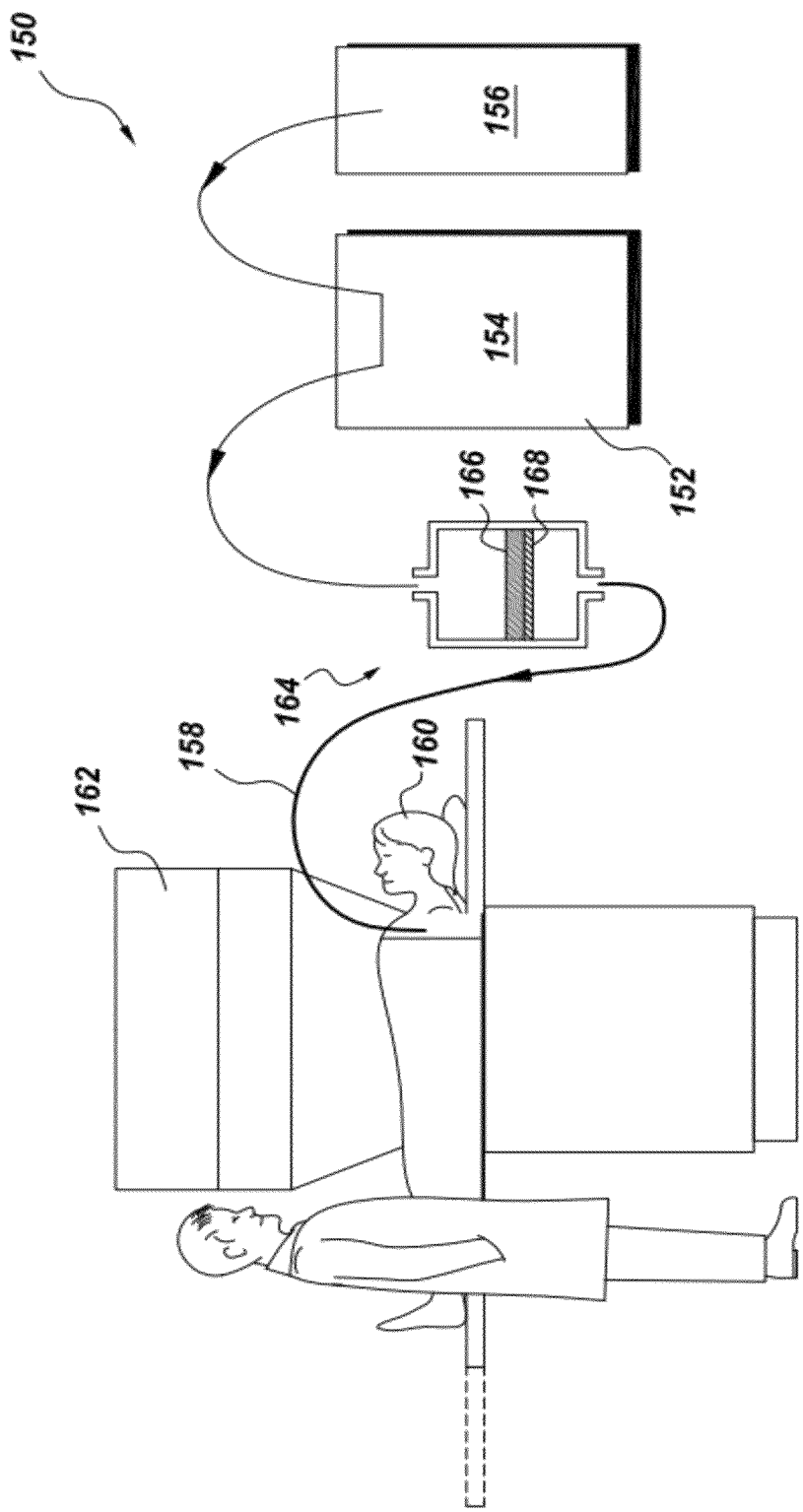
FIG. 11 is an illustration of an exemplary MRI system and filtering devices; in accordance with aspects of the present technique.

Referring to FIG. 11, an exemplary system 150 is shown for producing hyperpolarized samples for use in a MRI device and includes a cryostat 152 and polarizing subsystem 154 for processing material from a container 156 and resulting in the hyperpolarized material. A material delivery line 158 is used to deliver the hyperpolarized material to subject 160 within MRI scanner 162.

In the embodiment shown in FIG. 11, the hyperpolarized samples are used in an in vivo imaging application. It is to be appreciated that hyperpolarized samples may also be produced using the methods and techniques described below for Nuclear Magnetic Resonance (NMR) analysis. A filter 164 is attached to the delivery line 158 and positioned between the cryostat 152 and the subject 160 to filter the hyperpolarized material, before it is administered in the subject 160. The filter 164 includes a resin material 166 and a positioning material 168, as discussed above with regard to FIGS. 4-10. Although not illustrated, in some embodiments, two or more filters, such as filters 164 may be employed in series arrangement in the system 150. In these embodiments, the plurality of filters 164 may be arranged such that an output from one filter serves as an input for the adjacent filter in the direction of the subject 160. Each of the filters of the two or more filters may have either the same or different configurations, compositions of the resin, the positioning material and/or a diffuser.

Experimental

Initial experimentation was performed with a C18 functionalized; silica based chromatographic resins (YMC ODS-AQ). These results are summarized in Table 1. To provide baseline information regarding the capability of this filtration system multiple filter and solution states were explored. The three filter states investigated included (1) conditioned, (2) preconditioned, and (3) unconditioned. A condition filter was wetted with 100 mL ethanol followed by 200 mL deionized water at flow rates of 25 mL/min prior to use. A preconditioned filter was wetted with the same procedure as the conditioned filter, but the preconditioned filter was then frozen for at least 12 hours. The preconditioned filter was thawed and used without additional preparation. An unconditioned filter used resin in a dry state, as supplied by the manufacturer. Solution states included (1) neutral and (2) gradient. To test filter performance with a neutral solution all of the chemical components contained in a typical dissolution were mixed prior to filtration. The pH of this neutralized solution is approximately 7.6. The pH gradient was produced using a fluid path device wherein a volume, typically 50-60 mL of dissolution media (sodium hydroxide, TRIS, EDTA), was injected from a heated syringe (130° C.) into a cryogenically cooled vial containing pyruvic acid and EPA. At the beginning of the process, the pH of the solution, measured at the filter, is acidic, approximately a pH of 4. The pH then drops to a value of approximately 2 while the majority of the pyruvic acid is being dissolved. As the vial is emptied of pyruvic acid the pH of the solution increases to a pH of 12, corresponding to the pH of the dissolution media. This pH range (2-12 pH units) is outside of the specifications of most traditional chromatographic resins.

TABLE 1

Initial EPA Filtration Results

| Filter State | Solution State | Resin | Resin Mass | EPA Concentration |
|---|---|---|---|---|
| Conditioned | Neutral pH | YMC | 5 g | <1 µM |
| Preconditioned | Neutral pH | YMC | 5 g | 10 µM |
| Unconditioned | Neutral pH | YMC | 5 g | 250 µM |
| Conditioned | Gradient pH | YMC | 5 g | <1 µM |
| Preconditioned | Gradient pH | YMC | 5 g | 8 µM |
| Unconditioned | Gradient pH | YMC | 5 g | 170 µM |

Comparison was made at the relative scale of EPA filtration rather than the absolute values. As shown in Table 2, it was observed that with a conditioned filter EPA could successfully be removed from solutions that exhibited a neutral pH or a pH gradient. Replication of the conditioned filter exposed to a pH gradient was shown in replicate experiments (n=3) to generate a product containing 0.5±0.4 µM EPA and 101±4% of the injected pyruvate.

Figure 12:
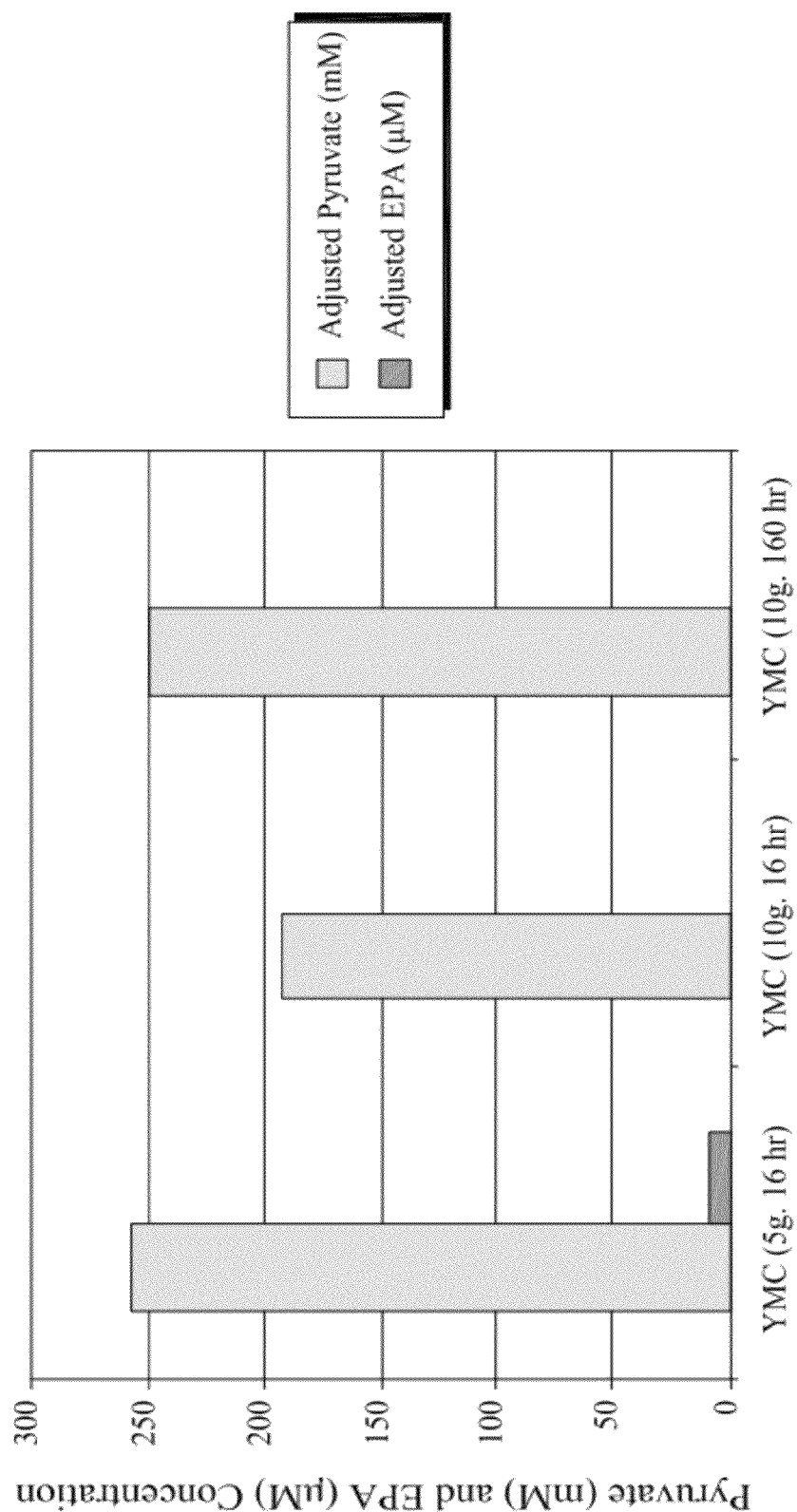
FIG. 12 is a graphical representation of the results of a baseline study to remove EPA from solutions with neutral pH or a pH gradient.

As a baseline, preconditioned filters were able to successfully remove the majority of the EPA from solutions with neutral pH or a pH gradient. The slightly degraded performance of the preconditioned filter relative to the freshly conditioned filter may be a result of either (1) phase collapse of the C18 resin during storage or thawing or (2) partial dewetting of the resin during thawing. Complete EPA removal was shown to be possible with and preconditioned filter with an enlarge resin bed (10 g vs. 5 g). To test the stability of the preconditioned filter (10 g resin) as a function of storage time filters that had been stored for 16 and 160 hr prior to use were compared. Both filters successfully removed all detectable EPA. Results of this study are presented in FIG. 12.

Unconditioned filters were found to perform poorly with solutions that exhibited either a neutral pH or a pH gradient. In both cases the majority of the EPA was no retained in the filter.

Resins with various functionalities were tested to remove EPA without prior conditioning are shown in Table 2. All resins were tested with the same dissolution conditions using the fluid path. Dissolution media (60 mL) was heated to 130° C. prior to injection. An injection pressure of 130 PSI, corresponding to a nominal flow rate of 300 mL/min, was used in most experiments. Higher injection pressure (200 PSI) was used in select studies where a flow restrictor was incorporated into the fluid path to increase pressure within the EPA filter. Filters contained 5 g of resin unless noted otherwise. Multiple parameters from the dissolution were measured including solution masses in various fluid path components before and after the dissolution, pHs and absorbances of solutions within the vial and receiver after the dissolution. In a gage study of the pH meter used in this study, the measurement standard deviation was 0.01 pH units. In gage studies of the absorbance spectrometer measurement standard deviations of 4 mM and 0.4 µM were calculated for pyruvate and EPA quantification, respectively. Resins were tested once for screening, resins that performed well were studied in more detail.

| Clarification of Original Table ||||||||
| Resin || Generic Composition | Physical Properties ||||
| Manufacturer | Trade Name | Functionality | Particle Size | Pore Size | Comment | Reference |
|---|---|---|---|---|---|---|
| YMC | ODS-AQ | C18/Silica | 50 um | 143 A | | 1 |
| Phenomenex | Sepra C18-T | C18/Silica | 58 um | 143 A | | 2 |
| Alltech | Large Pore C18 | C18/Silica | 50 um | 150 A | | 3 |
| Varian | Polaris | C18/Silica | | | Modified alkyl chains | 4 |
| Hamilton | PRP-3 | Polymeric | | | pH from 0-14 | 5 |
| Sorbent Tech | Dianion SP20SS | Styrene-based polymer | | | pH from 0-14 | 6 |
| Sorbent Tech | Dianion SP207SS | Brominated styrene-based polymer | | | pH from 0-14 | 7 |
| Alltech | C8 | C8/Silica | 50 um | 60 A | Shorter lipophilic chain | 8 |
| Phenomenex | Strata X | Modified styrene divinylbenzene polymer | | | Water wettable SPE resin | 3.9 |
| Varian | Abs Elut Nexus | Polymeric | | | Water wettable SPE resin | 10 |
| Waters | Oasis HLB | N-vinylpyrrolidone-Divinylbenzene copolymer | 50 um | 68 A | Water wettable SPE resin | 10.11 |
| Polymer Laboratory | PLRP-S 1000 | Styrene/divinylbenzene copolymer | | 1000 A | Large pore size | 12 |
| Polymer Laboratory | PLRP-S 4000 | Styrene/divinylbenzene copolymer | | 4000 A | Large pore size | 12 |

| Reference | Internet link |
|---|---|
| 1 | http://www.ymcamerica.com/columns/reversedphaseODS/ymcpackodsaq.htm |
| 2 | http://www.sudmed.ru/index.php?act=Attach&type=post&id=14061 |
| 3 | http://www.fishersci.com/ecomm/servlet/itemdetail?storeId=10652&langId=-1&catalogId=29104&productId=10323796&distype=0&fromSearch=0&hasPromo=0 |

| | | | | -continued | | | | |
|---|---|---|---|---|---|---|---|---|
| 4 | http://www.chem.agilent.com/en-US/products-services/Columns-Sample-Preparation/LC-LC-MS-Columns/Analytical-HPLC-UHPLC/Polaris/Pages/default.aspx | | | | | | | |
| 5 | http://www.phenomenex.com/Info/WebDocumentServe/chromtips.pdf | | | | | | | |
| 6 | http://www.sorbtech.com/chromatography/adsorbents/polymeric-resins/mitsubishi-resins/synthetic-adsorbents/synthetic-adsorbent-for-chromatography-separation/ | | | | | | | |
| 7 | http://www.sorbtech.com/chromatography/adsorbents/polymeric-resin/mitsubishi-resins/synthetic-adsorbents/ | | | | | | | |
| 8 | http://www.witko.com.pl/attach/zalacznikipz/chromatografia/kolumny lc/grace/alltech platinum.pdf | | | | | | | |
| 9 | https://phenomenex.blob.core.windows.net/documents/e62d67d8-eef5-42f0-b829-4e188661ab57.pdf | | | | | | | |
| 10 | http://www.sciencedirect.com/science/article/pii/S0021967303019083 | | | | | | | |
| 11 | http://www.waters.com/webassets/cms/category/doc/Oasis%20HLB%20Disk%20product%20introduction.pdf | | | | | | | |
| 12 | http://www.chem.agilent.com/Library/selectionguide/Public/5990-9384EN.pdf | | | | | | | |

Clarification of Original Table (with additional physical property info shaded green)

| Resin | | | Generic Composition | Physical Properties | | | | Comment | Reference |
|---|---|---|---|---|---|---|---|---|---|
| Manufacturer | Trade Name | | Functionality | Particle Size | Pore Size | Surface Area | Carbon Load | | |
| YMC | ODS-AQ | | C18/Silica | 50 μm | 120-200 A | | 10-14% | | 1 |
| Phenomenex | Sepra C18-T | | C18/Silica | 50-58 μm | 135-143 A | 300 m2/g | 15% | | 2 |
| Altech | Large Pore C18 | | C18/Silica | 50 μm | 150 A | | 14% | | 3 |
| Varian | Polaris | | C18/Silica | 10 μm | 180 A | 200 m2/g | 13.80% | Modified alkyl chains | 4 |
| Hamilton | PRP-3 | | C18/Silica | 10 μm | 300 A | | | pH from 0-14 | 5 |
| Sorbent Tech | Dianion SP20SS | | Styrene-based polymer | 50-100 μm | 290-450 A | 560 m2/g | | pH from 0-14 | 6 |
| Sorbent Tech | Dianion SP207SS | | Brominated styrene-based polymer | 63-150 μm | 110-210 A | 600 m2/g | | pH from 0-14 | 7 |
| Altech | C8 | | C18/Silica | 50 μm | 60 A | 200 m2/g | 4% | Shorter lipophilic chain | 8 |
| Phenomenex | Strata X | | Modified styrene divinylbenzene polymer | 33 μm | 85 A | 800 m2/g | | Water wettable SPE resin | 3.9 |
| Varian | Abs Elut Nexus | | Polystyrene-methacrylate | 50-80 μm | | 500-650 m2/g | | Water wettable SPE resin | 10 |
| Waters | Oasis HLB | | N-vinylpyrrolidone-Divinylbenzene copolymer | 30-50 μm | 680 A | 610 m2/g | | Water wettable SPE resin | 10,11 |
| Polymer Laboratory | PLRP-S 1000 | | Styrene/divinylbenzene copolymer | 10-30 μm | 1000 A | | | Large pore size | 12 |
| Polymer Laboratory | PLRP-S 4000 | | Styrene/divinylbenzene copolymer | 10-30 μm | 4000 A | | | Large pore size | 12 |

| Reference | Internet link |
|---|---|
| 1 | http://www.ymcamerica.com/columns/reversedphaseODS/ymcpackodsaq.htm |
| 2 | http://www.sudmed.ru/index.php?act=Attach&type=post&id=14061 |
| 3 | http://www.fishersci.com/ecomm/servlet/itemdetail?storeId=10652&langId.=-1&catalogId=29104&productId=10323796&distype=0&fromSearch=0&hasPromo=0 |
| 4 | http://www.chem.agilent.com/en-US/products-services/Columns-Sample-Preparation/LC-LC-MS-Columns/Analytical-HPLC-UHPLC/Polaris/Pages/default.aspx |
| 5 | http://www.phenomenex.com/Info/WebDocumentServe/chromtips.pdf |
| 6 | http://www.sorbtech.com/chromatography/adsorbents/polymeric-resins/mitsubishi-resins/synthetic-adsorbents/synthetic-adsorbents-for-chromatography-separation/ |
| 7 | http://www.sorbtech.com/chromatography/adsorbents/polymeric-resins/mitsubishi-resins/synthetic-adsorbents/ |
| 8 | http://www.witko.com.pl/attach/zalacznikipz/chromatografia/kolumny lc/grace/alltech platinum.pdf |
| 9 | https://phenomenex.blob.core.windows.net/documents/e62d67d8-eef5-42f0-b829-4e188661ab57.pdf |
| 10 | http://www.sciencedirect.com/science/article/pii/S0021967303019083 |
| 11 | http://www.waters.com/webassets/cms/category/docs/Oasis%20HLB%20Disk%20product%20introduction.pdf |
| 12 | http://www.chem.agilent.com/Library/selectionguide/Public/5990-9384EN.pdf |

Resins were selected to cover a range of surface functionality and substrate materials. Several traditional C18-based silica resins, similar to the benchmark YMC ODS-AQ resin, were studied as potential cost or availability alternatives. Experiments with the Phenomenex Sepra C-18-T resin showed that this resin significantly altered the pH of the dissolution product resulting in a low pH in the receiver vessel. This may be related to interaction of the unprotected silica surface of the resin with the high pH dissolution media seen at the end of an injection; most silica-based resins have pH range limited to values less than 8 due to manufacturer dependent silica surface chemistry. Slight differences in manufacturer dependent surface chemistry may result in the differences in performance between the YMC and Alltech C18-based silica resins.

Figure 13:
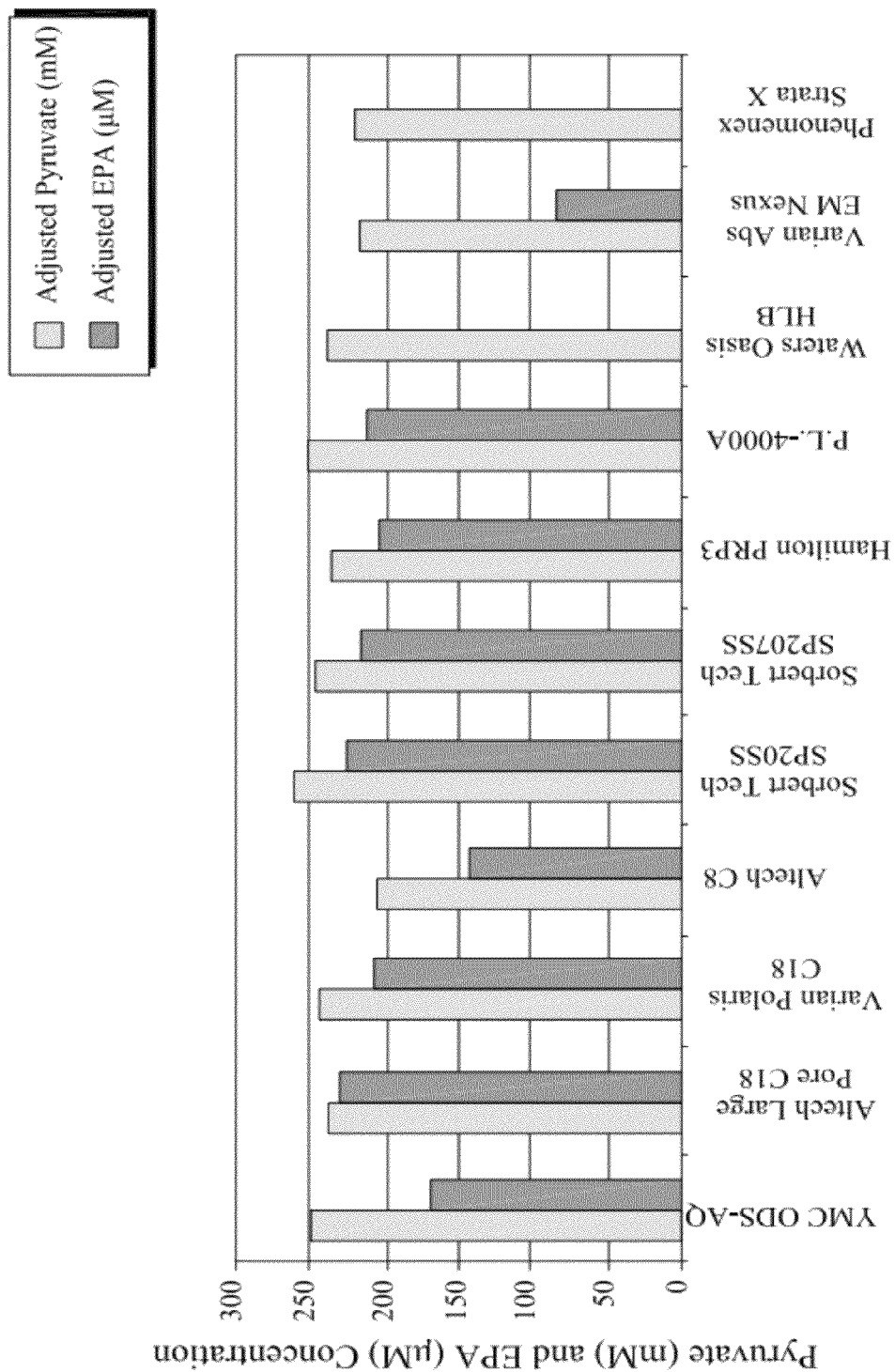
FIG. 13 is a graphical representation of filtration efficiency using various resins.

As shown in FIG. 13, the YMC and Alltech C18 resins exhibited poor EPA removal characteristics, but did not retain pyruvate. The YMC resin, which performed better than the Alltech resin, removed approximately 30% of the EPA. Varian Polaris is also a C18-based silica resin, but the alkyl chains have been modified to allow for use with 100% aqueous solution over a wide pH range. The Varian Polaris resin performed poorly, retaining little of the EPA. Although the Varian Polaris is reported to be stable in 100% aqueous solutions, it was not water wettable, meaning that traditional alcohol conditioning procedures are typically employed before use.

As shown in FIG. 13, a shorter lipophilic chain resin was also evaluated. An Alltech C8-based silica resin demonstrated similar EPA removal efficiency as compared to the YMC C18 resin and better performance than the Alltech C18 resin. This C8-based resin was also found to retain pyruvate to a greater extent than the C18 resins.

Polymeric resins are known to operate over a broader pH range than traditional silica-based resins. For this reason, several polymeric resins were evaluated. Several of the resins including Waters Oasis HLB, Varian Abs Elut Nexus and Phenomenex Strata X are as water wettable. As is seen in FIG. 13, EPA filtration efficiency of polymeric resins varied significantly. Sorbent Technologies, Hamilton and Polymer Laboratories resins performed poorly, retaining less than 20% of the available EPA. The water wettable polymeric resins performed quite well, with EPA retention ranging from 67 to >99%. Both the Waters Oasis HLB and Phenomenex Strata X retained >99% of the measurable EPA while passing 90 to 100% of the pyruvate to the receiver vessel. In replicate experiments with 5 g of the Waters Oasis HLB resin receiver vessel concentrations of pyruvate and EPA were found to be 235±5 mM and 0.0±0.2 µM, respectively.

It has been suggested (Nagae, N; Enami, T; Doshi, S. LC-GC North America 2002, 20, 964) that the application of significant pressures to the chromatographic column, on the order of 3000 PSI for typical small pore resins (<100 Å), allows traditional C18-based silica resins to operate with 100% aqueous solution. Although the use of such high operating pressures may not be desired in the filtration process described, the Laplace-Young equation (Equation 1) shows that the pressure differential required to maintain resin activity scales linearly with pore diameter.

Figure 14:
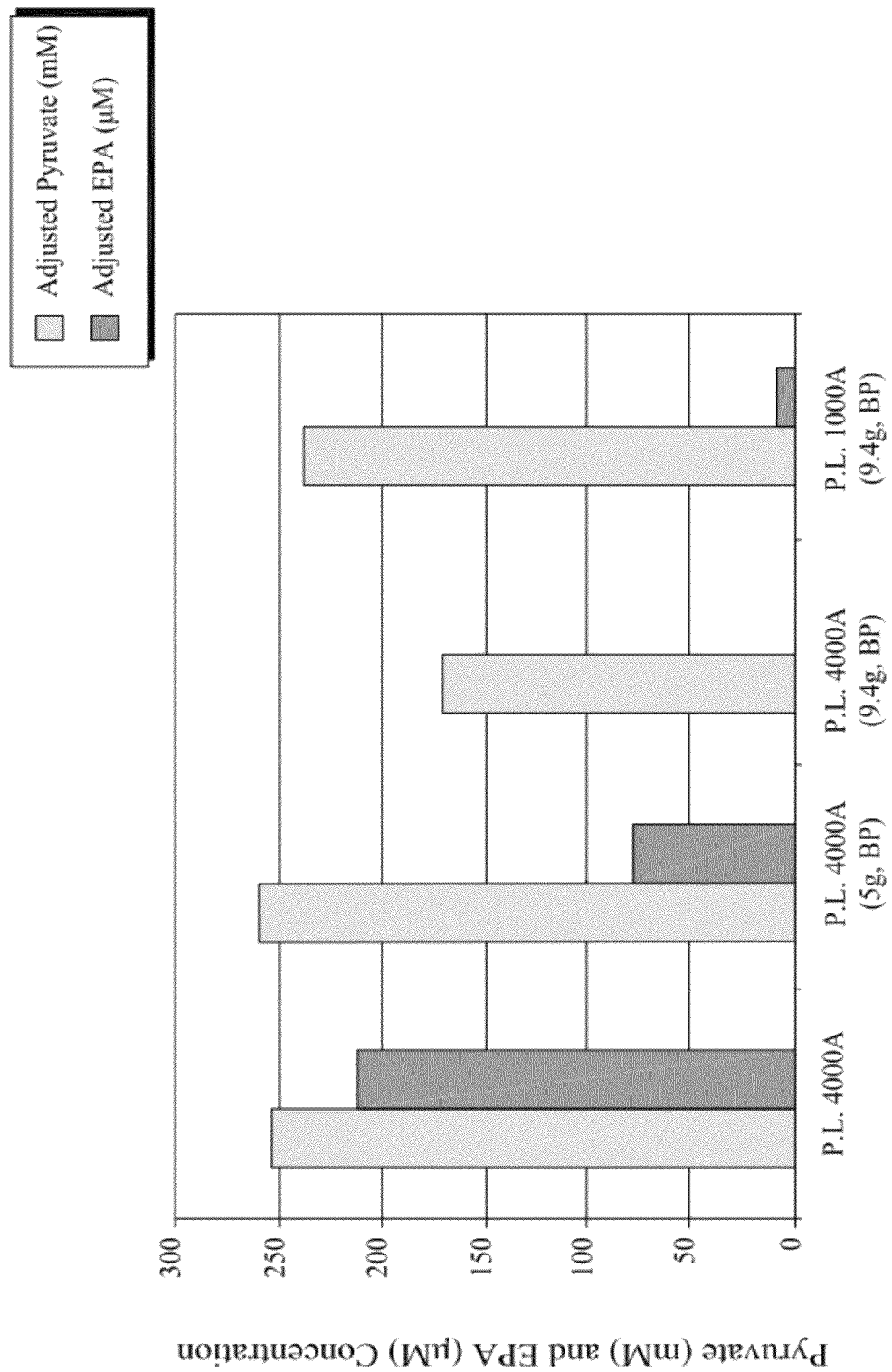
FIG. 14 is a graphical representation filtration efficiency using giga-pore resins.

As such, two giga-pore (>1000 Å) resins (Polymer Laboratories PLRP-S 4000 and PLRP-S 1000, Polymer Laboratories Ltd, Shropshire, UK)) were evaluated. As shown in FIG. 14, in the absence of a significant back pressure (on the order of 200 PSI), the PLRP-S 4000 resin performed poorly, retaining less than 20% of the available EPA. The addition of a flow restrictor immediately after the EPA filter to generate elevated pressures within the filter resulted in a significant improvement in resin performance, retaining approximately 67% of the available EPA. By increasing the resin bed length to 9.4 g, the EPA filtration efficiency was improved to >99%. With this extended resin bed, an increase in pyruvate retention, approximately 30% was also noted. An extended bed length (9.4 g) of the Polymer Laboratories PLRP-S 1000 resin operated with a similar back pressure retained 95% of the available EPA while passing 95% of the pyruvate to the receiver vessel.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A method of filtering an unrefined pharmaceutical product, comprising:
   mixing a buffer, a chelator, and a basic medium with the unrefined pharmaceutical product to form a filtering mixture, wherein said unrefined pharmaceutical product comprises a pharmaceutical product and an electron paramagnetic agent (EPA) frozen into a solid state, wherein the filtering mixture has a pH that changes from acidic to basic or from neutral to basic as the EPA thaws, and wherein the EPA includes a soluble component and an insoluble component in amounts that vary as the pH of the filtering mixture changes;
   providing a filtering device including a bed of resin configured to selectively adsorb the soluble component of EPA from the filtering mixture, wherein the bed of resin includes an upstream side and a downstream side, an upstream positioning material disposed adjacent to upstream the upstream side of the bed of resin, a downstream positioning material positioned adjacent the downstream side of the bed of resin, the upstream positioning material defining an upstream side, wherein the downstream positioning material is configured to provide mechanical support to the the bed of resin to retain the resin in position, wherein the upstream positioning material is configured to retain the insoluble component of the EPA on the upstream side thereof, and wherein the resin is adapted to adsorb the soluble component of the EPA from the filtering mixture as the pH of the filtering mixture changes during the filtration process from acidic to basic, or from an acidic to a neutral pH;
   passing the filtering mixture through the upstream positioning material, through the bed of resin, and through the downstream positioning material of the filtering device;
   adsorbing the soluble component of the EPA with the resin; and
   retaining the insoluble component of the EPA on an upstream side of the upstream positioning material.

2. The method of claim 1 wherein the resin is silica-based a functionalized silica-based, polymeric resin or a combination thereof.

3. The method of claim 2 wherein the functionalized silica based resin is a C18 based silica resin, C8 based silica resin, or a combination thereof.

4. The method of claim 2 wherein the polymeric resin comprises a divinylbenzene copolymer.

5. The method of claim 1, wherein the basic medium comprises sodium hydroxide, and wherein the buffer comprises tris(hydroxymethyl)-aminomethane.

6. The method of claim 1, further comprising configuring the bed of resin to retain a portion of the insoluble component that is not retained by the upstream positioning material, and retaining the portion of the insoluble component of EPA that is not retained by the upstream positioning material on the upstream side of the bed of resin with the bed of resin.

7. The method of claim 1, wherein a flow rate of the mixture at the filtering device is in a range from about 3 mL/s to about 12 mL/s.

8. The method of claim 1, wherein a pore size of the resin is in a range from about 60 Å to about 4000 Å.

9. The method of claim 1, wherein a pore size of the positioning material is in a range from about 5 micrometers to about 30 micrometers.

10. The method of claim 1, wherein the pharmaceutical product comprises pyruvic acid.

\* \* \* \* \*